(12) United States Patent
Lampert et al.

(10) Patent No.: US 6,865,519 B2
(45) Date of Patent: Mar. 8, 2005

(54) REACTION MEASUREMENT METHOD AND SYSTEM

(75) Inventors: Shlomo Lampert, Jerusalem (IL); Shmuel Stashevsky, Petah-Tikvah (IL)

(73) Assignee: Assessment Systems, Ltd., Jerusalem (IL)

( * ) Notice: Subject to any disclaimer, the term of this patent is extended or adjusted under 35 U.S.C. 154(b) by 0 days.

(21) Appl. No.: 10/398,648

(22) PCT Filed: Oct. 4, 2001

(86) PCT No.: PCT/IL01/00926

§ 371 (c)(1),
(2), (4) Date: Apr. 8, 2003

(87) PCT Pub. No.: WO02/30260

PCT Pub. Date: Apr. 18, 2002

(65) Prior Publication Data

US 2004/0044495 A1 Mar. 4, 2004

(51) Int. Cl.[7] .......................... A61B 19/00; G09B 7/00
(52) U.S. Cl. ........................................ 702/189; 600/301

(58) Field of Search ................................ 600/300–301, 600/587, 595; 235/70 A; 434/323–324; 702/188, 189

(56) References Cited

U.S. PATENT DOCUMENTS

| | | | | |
|---|---|---|---|---|
| 5,873,900 A | * | 2/1999 | Maurer et al. | ................. 607/46 |
| 6,033,365 A | * | 3/2000 | von Zitzewitz | ............. 600/300 |
| 6,258,042 B1 | * | 7/2001 | Factor et al. | ................ 600/557 |
| 6,334,778 B1 | * | 1/2002 | Brown | ......................... 434/258 |

* cited by examiner

Primary Examiner—Marc S. Hoff
Assistant Examiner—Paul L Kim

(57) ABSTRACT

A method for measuring a subject's reaction to stimuli presentation by using a measurement scale, the method including the steps of presenting the subject with stimuli and the measurement scale, enabling the subject to indicate his reaction by moving the position of the scale with reference to time, tracing and recording the scale positions and movements as function of time and detected measurement events, detecting the final scale position, and evaluating and analyzing the measurement data in order to determine the subject's reaction to the stimuli.

21 Claims, 5 Drawing Sheets

REACTION MEASUREMENT METHOD AND SYSTEM

CROSS-REFERENCE TO RELATED APPLICATIONS

This application is a U.S. National Phase Application under 35 U.S.C. 371 of PCT International Application No. PCT/IL01/00926, which has an international filing date of Oct. 4, 2001, and which claims priority from Israel Patent Application No. IL 138955, filed Oct. 11, 2000.

BACKGROUND OF THE INVENTION

The present invention relates to a method and system for measuring subject's reaction to stimuli. More specifically the present invention relates to a method and system engaged in measurements of human reaction and analysis thereof.

In many fields such as psychology, sociology, political science, social work, marketing, management, decision making, education, medicine etc. There is a need to identify and/or measure reactions of subjects toward objects, events, situations, issues, states, people, etc.

The term "reaction to stimuli" as used herein is intended to connote the subject's indication of attitude, opinion, judgement, preference, evaluation, satisfaction, involvement, feeling, intention, etc. when presented with a question/statement/situation or a problem, with or without additional stimuli, the subjective response to which is sought to be measured.

Four basic types of measurement scales are used in measuring human reactions. One of the scales is the Nominal Scale which enables the assignment of elements to different categories, numerical values that may be assigned to them are of no meaning except for category identification.

A second scale is the Ordinal Scale in which it is possible to assign elements to categories or classes, where the categories or classes establish a monotonic increasing or decreasing function.

A third scale is the Interval Scale in which the elements are assigned values along a defined continuum, e.g., like—dislike. Numbers represent points on the continuum, where differences in evaluation of attributes, factors or variables are represented by the differences between the numbers (in any pre-selected units of measurements). This scale does not possess an absolute zero point, thus no ratios are allowed, e.g. in measurement of temperature using Fahrenheit or Centigrade degrees, one can relate to temperature differences, and but to temperature ratios.

The fourth type of scale is the Ratio Scale in which the elements are assigned values on a continuum where an absolute zero does exist. Thus all arithmetic operations are permissible with these values including ratios, e.g. income, height, etc.

Based on the above four scales many measurement techniques were developed where they represent modified forms of these basic scales.

Of great importance within measuring subject's reaction to stimuli is the measurement of intervening variables, i.e., the variables which link the reality in which the individual exists with his subjective responses or behavior. Such intervening variables include motivations, perceptions, cognition, attitudes, involvement, opinions, judgements, preferences, evaluations, feelings, intentions, satisfactions etc.

Since these variables are on the whole subjective and situational, an absolute zero point does not apply in most of them. Thus, the ratio scale, for all practical purposes, is of lesser value in said measurements. For variables for which there is no theoretical constraints for the use of values on a continuum, but which do not have an absolute zero point, the most sophisticated scale analytically, and the one for which most of the current statistical tools have been developed, is the interval scale. However, a large percentage of the general population finds it difficult and sometimes impossible to place themselves on an interval scale, since it is extremely difficult for people to express an opinion on a continuum as presented to them by prior art techniques wherein the subject must designate a point between two poles as representing his position relative to the values represented by said poles. Rather, the ordinal scale seems to most people as a scale to which it is easier for them to relate, yet it provides only a limited number of choices, usually between 5–7, and the statistical analysis of such data is quite limited.

According to prior art of U.S. Pat. No. 4,337,391 (hereinafter the "Lampert patent") there has been a proposed device, which combines the desired statistical properties of the interval (and ratio) scales with the ease of measurement of the ordinal scale. Lampert patent device enables measuring a subject's reaction to stimuli comprising of a first means having a defined viewing area and a colored means with at least one colored area adapted to be viewed in said viewing area, wherein the extent of colored area viewable is variable and adapted to indicate the degree of a subject's reaction to specific stimuli; and wherein there is a means for translating the extent of said colored area viewed in said viewing area into a scaled value which corresponds to said extent of colored area, and where said scaled value is being operatively arranged so as not to be visible to the subject when viewing said viewing area. The measuring device can be used for different purposes of evaluating human reaction(s) toward stimuli, such as: conducting polls, evaluating decisions of one or many participants, measuring consumer attitude toward products or services, measuring student reactions to a learning experience, etc.

The use of Lampert device for measuring human reactions suffers from several deficiencies. First, each subject (person) must be provided with a Lampert device. Second, the reaction measurement demands a personal contact with the subject, and in most cases a human operator for recording the numerical value. This process can cause human errors, measurement bias, and in a period where personal interviews are becoming less popular, it may result in a limited number of measurements. Finally, in the Lampert device the measurements of the subject reaction to stimuli are restricted to his final reaction, ignoring the subject's intermediary (in-between) reactions through the process of making up his mind, which can be of great value to the researcher and/or to the research sponsor. Examination of the process can indicate degree of hesitation, determination, intensity of feelings, etc.

The prime object of the invention, therefore, is to provide a reaction measurement method and system enabling to measure subject in-between, temporary reactions before reaching his final reaction.

It is a further object of the invention to provide a computerized reaction measurement method and system enabling an efficient way of gathering and analyzing the reactions of a large number of subjects having computerized devices.

It is another object of the invention to provide a computerized reaction measurement method and system enabling immediate evaluation and/or analysis of subject's reaction and conveying further stimuli to the subject based upon this evaluation and/or analysis.

SUMMARY OF THE INVENTION

BRIEF DESCRIPTION OF THE DRAWINGS

These and further features and advantages of the invention will become more clearly understood in the light of the ensuing description of a preferred embodiment thereof, given by way of illustration only, with reference to the accompanying drawings, wherein.

DETAILED DESCRIPTION OF THE PREFERRED EMBODIMENTS

Figure 1:
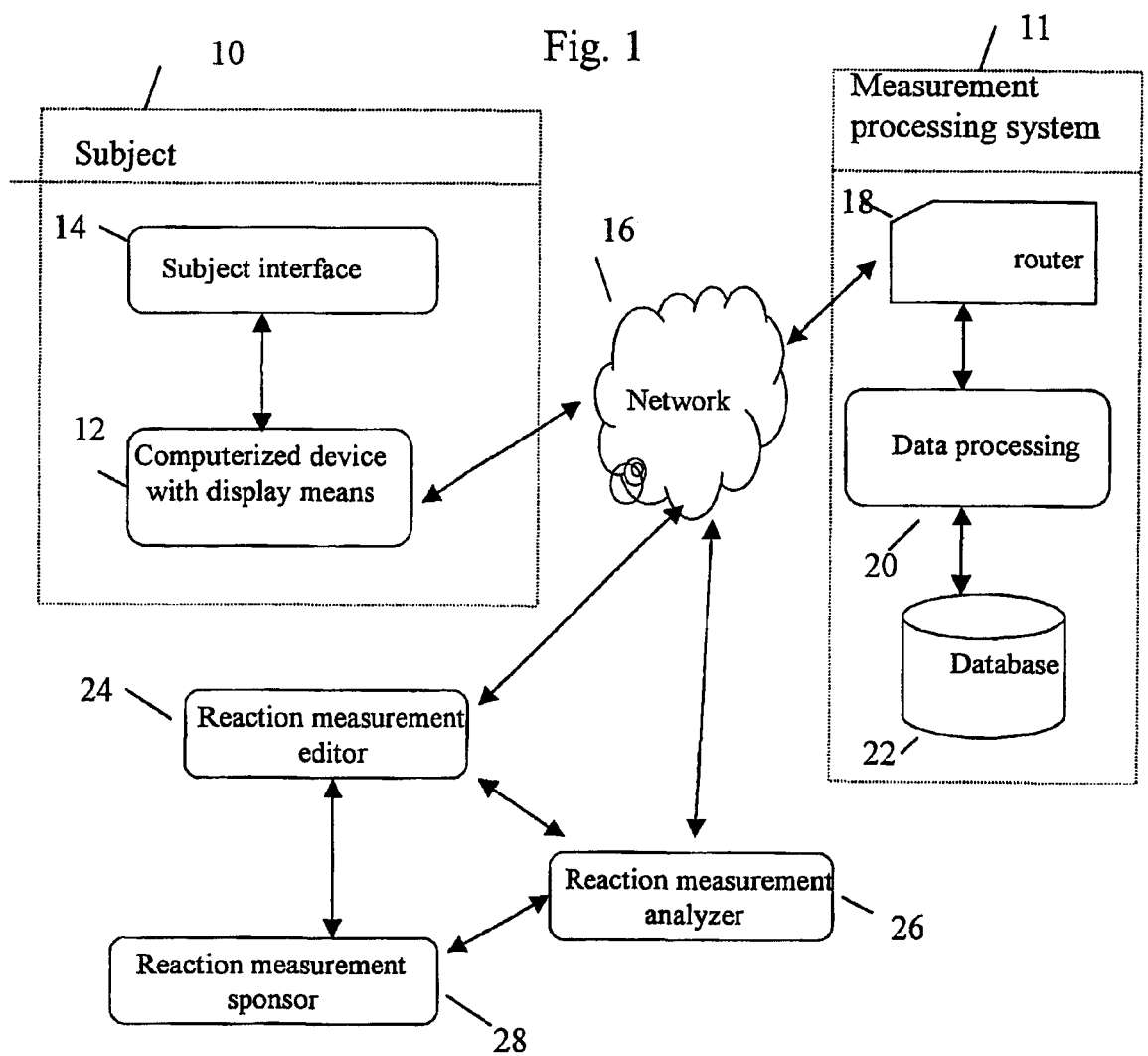
FIG. 1 is a general diagrammatic representation of the environment in which the present invention is practiced.

Referring to FIG. 1 of the drawings, it will be seen that a Reaction measurement editor 24 composes a set of stimuli and questions/statements/situations to which the subject's reaction is sought to be measured. This set is stored in the Measurement processing system 11. The editor's work can be initiated by any Reaction measurement sponsor 28 having an interest in performing such measurements.

Each subject 10 has a Computerized device with display means 12 and subject interface 14, connected to a Router 18 via network 16 in a conventional manner. Subject 10 is provided with stimuli and/or questions/statements/situations ("Stimuli") transmitted by the Measurement processing system 11 via the network 16. The measurement software application of the subject can be stored in his computerized device and/or transmitted to the subject with the stimuli from the Measurement processing system 11. The subject's reactions are measured using the measurement software application and transmitted via the Network 16 to the Measurement processing system. The measurement data of subjects are gathered in the Measurement processing system to be processed, evaluated, and/or analyzed by the Reaction measurement analyzer 26.

These measurements can serve various purposes such as conducting polls, following decision making processes, and evaluation of human reactions toward different stimuli, such as: consumer attitude to products or services, student reactions in learning processes, etc.

Figure 2:
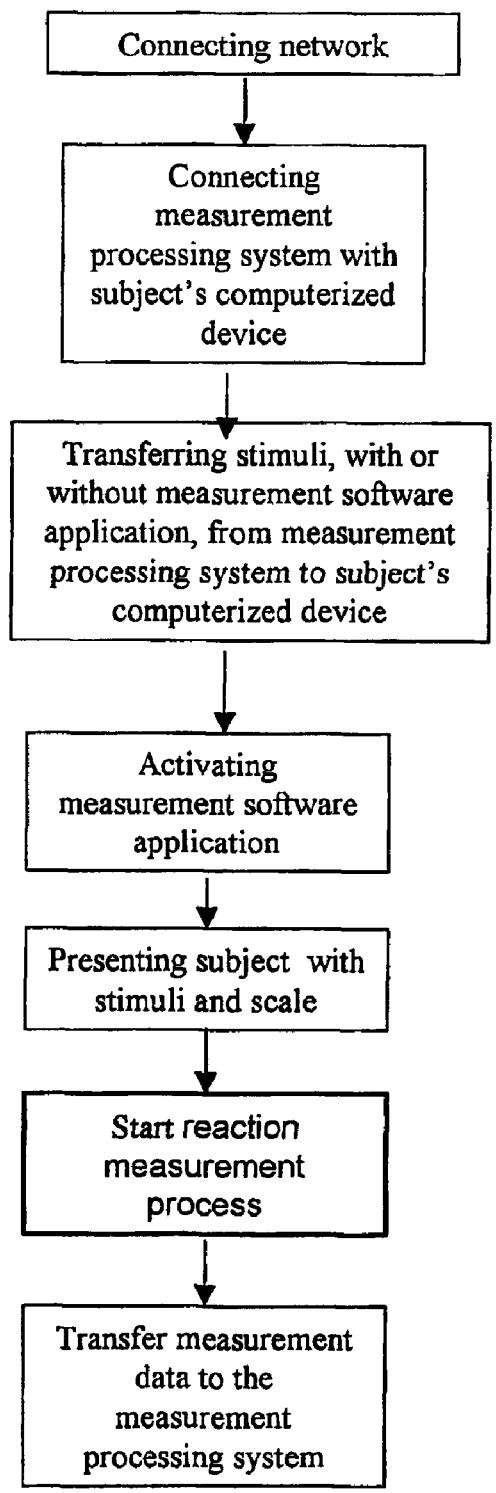
FIG. 2 is a flowchart of measuring subject reaction to stimuli according to the present invention.

FIG. 2 illustrates the process of exposing subject(s) to stimuli, through computerized device(s) while activating the measurement software application. Once the subject is supplied with new stimuli, he is asked to respond to those stimuli and/or to questions/statements regarding the stimuli either instantly—in real time—or at later stage—in his free time. The process of conducting the measurements can take place regardless of whether or not the subject is connected to the network at that point in time, since the reactions of the subject can be temporarily stored in the computerized device and conveyed to the measurement processing system via a router 18 at the next time the subject connects to the network. The stimuli data can be transferred in Push (sponsor initiated) or Pull (subject initiated) mode, by e-mail, Internet, telephone, or any other communication means.

Figure 3:
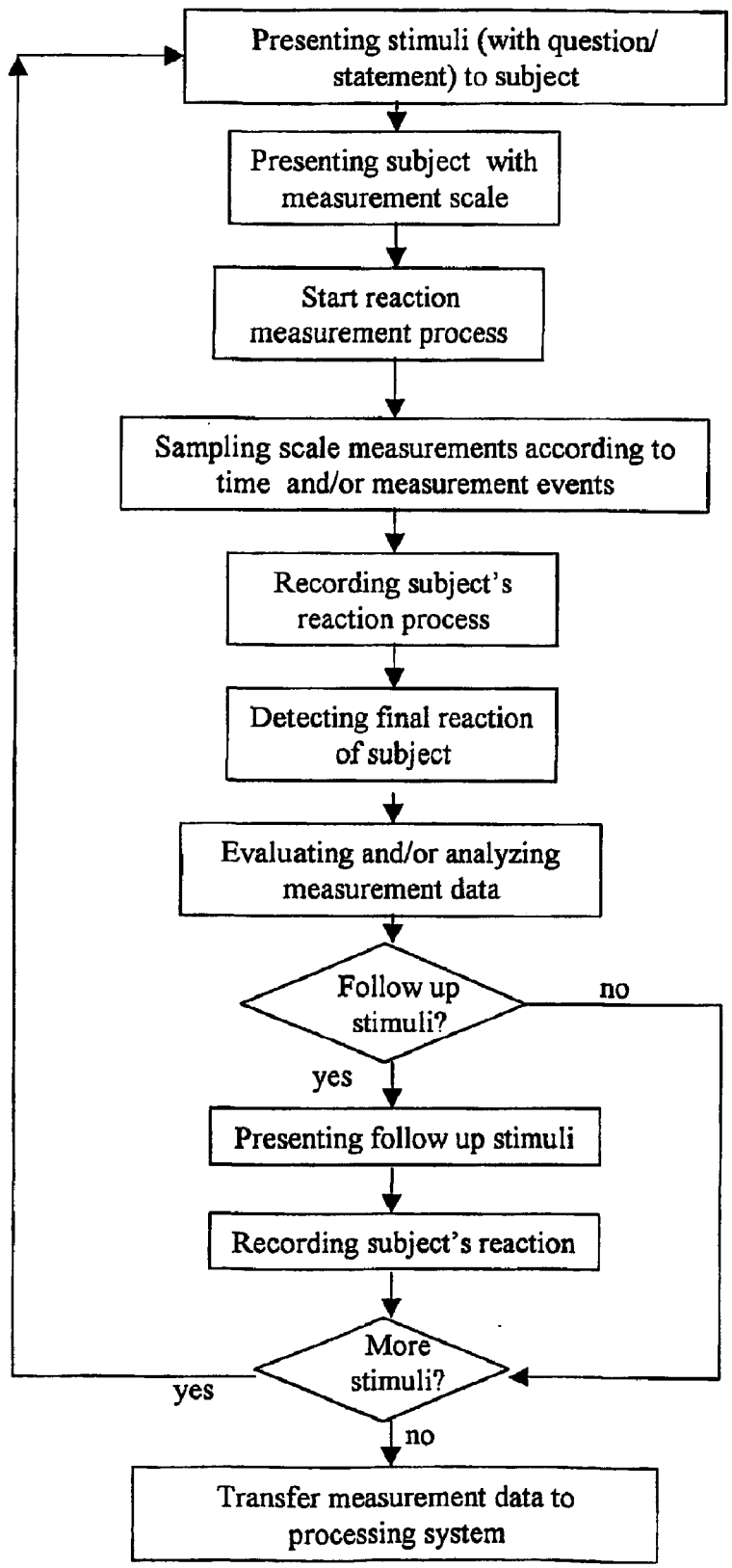
FIG. 3 is a flowchart of processing a computerized questionnaire to measure subject's reaction to stimuli according to the present invention.
Figure 4:
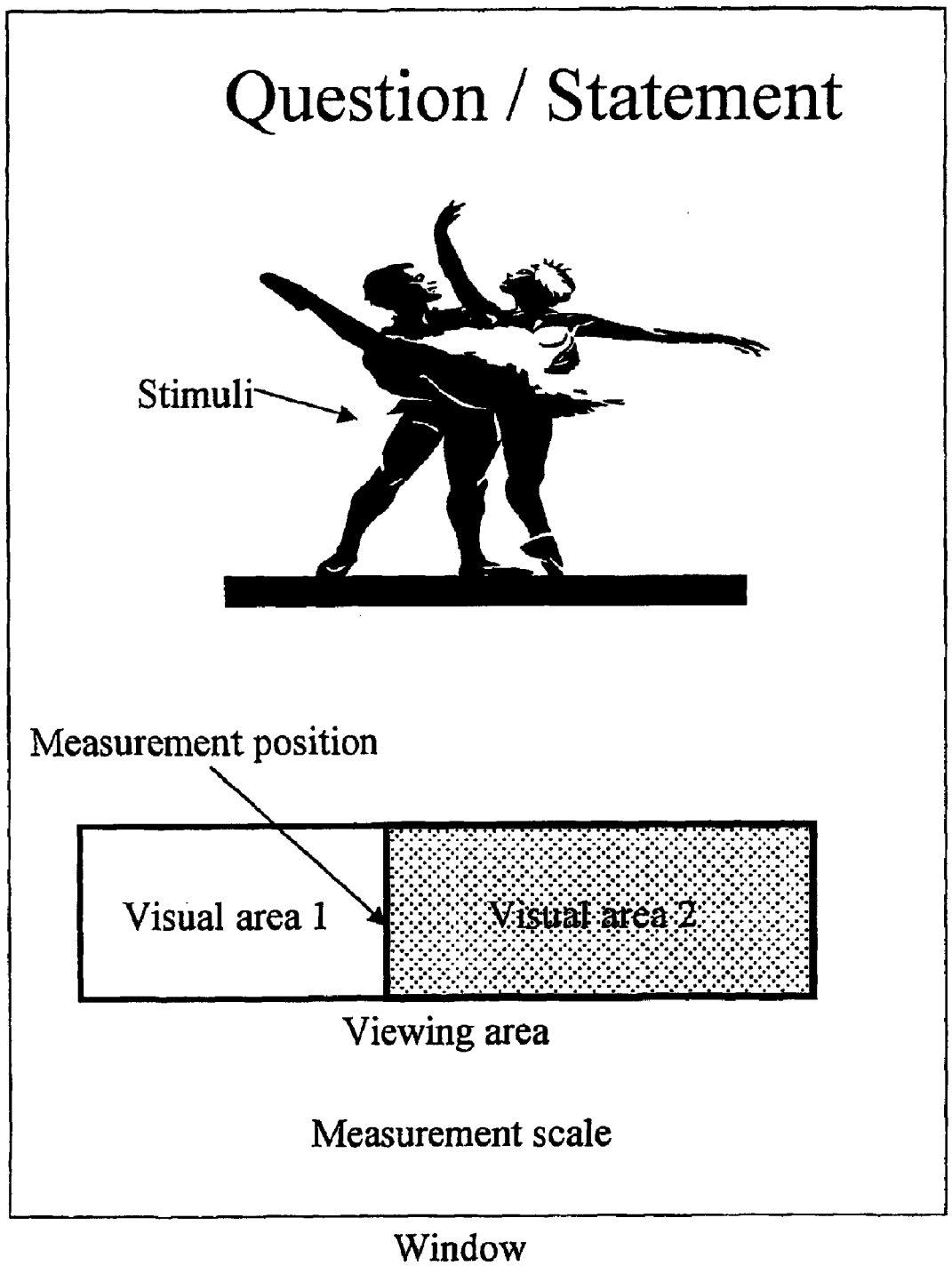
FIG. 4 is an illustration of question/statement, stimuli and measurement scale presentation.

The subject's reaction measurement process is illustrated in FIG. 3. The subject is presented with stimuli within a window within the displaying means, as illustrated in FIG. 4. At the top of the window the question/statement is displayed and/or vocally expressed, and the relevant stimuli is presented below. The measurement scale is displayed at the bottom of the window. The subject can set the scale's position by applying any interface—input device (mouse, joystick, keyboard keys, buttons, pen, touch, voice, eye movement, etc.). The scale can be continuous or partly continuous according to the characteristics of input device, the computerized device, and/or the relevant issue in question.

The scale can be represented in different modes, one of the preferred option is illustrated in FIG. 4, displaying a polygon frame, e.g. a rectangular viewing area, having two different visual areas represented at least by one color or pattern, where each color or pattern is variable in relation to the viewing area representing a proportional area size, from 0 percent to a 100 percent, and the relative proportions of the colors or patterns at any point in time are controlled by the subject to visually express his reaction to the stimuli at that point in time. A visual area with one color/pattern, complemented by a visual area with a neutral background is applied when the measurement involves one dimension/pole, such as involvement, pain etc. Two colors/patterns are applied when the measurement involves two dimensions/poles, such as attitude (positive/negative), preference (two alternatives) etc. The stimuli can be any multimedia object, e.g. an image portrait of a presidential candidate, video clip, audio playback, smell, etc.

The subject can set the scale position, defined by the location of the boundary line separating the two visual areas (the "measurement position"), by controlling the proportion of each visual area size. This can be done by applying an interface—input device for moving the location of the measurement position along the viewing area to visually express the subject's reaction to stimuli.

Once the window is presented to the subject and the question/statement is expressed, a timer is started and continues to operate throughout the measurement period. During this time period the subject may hesitate, move the measurement position to yield different proportion of the visual areas until he reaches his final reaction. The measurement software application, via operating system, records the subject's reaction as reflected by the movement of the measurement position within the rectangular viewing area throughout the above measurement period. Alternatively, the measurements can be sampled according to "measurements events" involving a change in the course of moving the measurement position, e.g. a change of direction or rate of movement.

In each measurement sampling the relative proportion of the area size of each color/pattern is measured and recorded by an equivalent numerical value, as well as its respective point in time i.e. resulting in scale and time positions. All recorded scale positions and their respective times are stored in the computerized device memory with reference to the displayed question/statement and stimuli. Once the subject reaches his final decision, e.g. by clicking "next", "forward" or "end", the final measurement is stored, with reference to its scale's position and its corresponding point in time. "Measurements data" is composed of a string of measurements sampling values representing complete response process(es) of the subject to one or more questions/statements or to a complete questionnaire or survey.

The initial position of the color/pattern proportions may be at the midpoint, at one of the leftmost or rightmost positions of the viewing area, or at any other arbitrary point along the scale. The choice of the initial position is selected by the Reaction measurement editor with reference to the type of question/statement characteristics. Moreover, the colors/patterns can be fixed for all questions/statements/stimuli or changeable according to the editor choice adapted to the type of stimuli measurement, number of dimensions/poles, culture or other environmental influence. The window may not be limited to one question/statement, rather in some cases the editor may prefer to present the subject with a full set of questions/statements regarding a common issue, e.g. in a pre-election public opinion poll regarding competing candidates it is possible to measure subject's response using a separate scale for each candidate, where all scales may be shown together in the window.

An alternative measurement scale can be represented by a pendulum, where the pendulum arm represents the movement position within the defined viewing area, and the subject can control the position of the pendulum arm to indicate his reaction to questions/statements and/or stimuli.

A further alternative measurement scale can be represented by a balanced equilibrium system. The state of the equilibrium is represented by the balance position between two visual areas state (e.g. the visual area state is represented by its color or pattern), wherein a change in one visual area state result a proportional change of the second visual area state e.g. connected vessels. The subject can control the position of the equilibrium state to indicate his reaction to questions/statements and/or stimuli.

Figure 5:
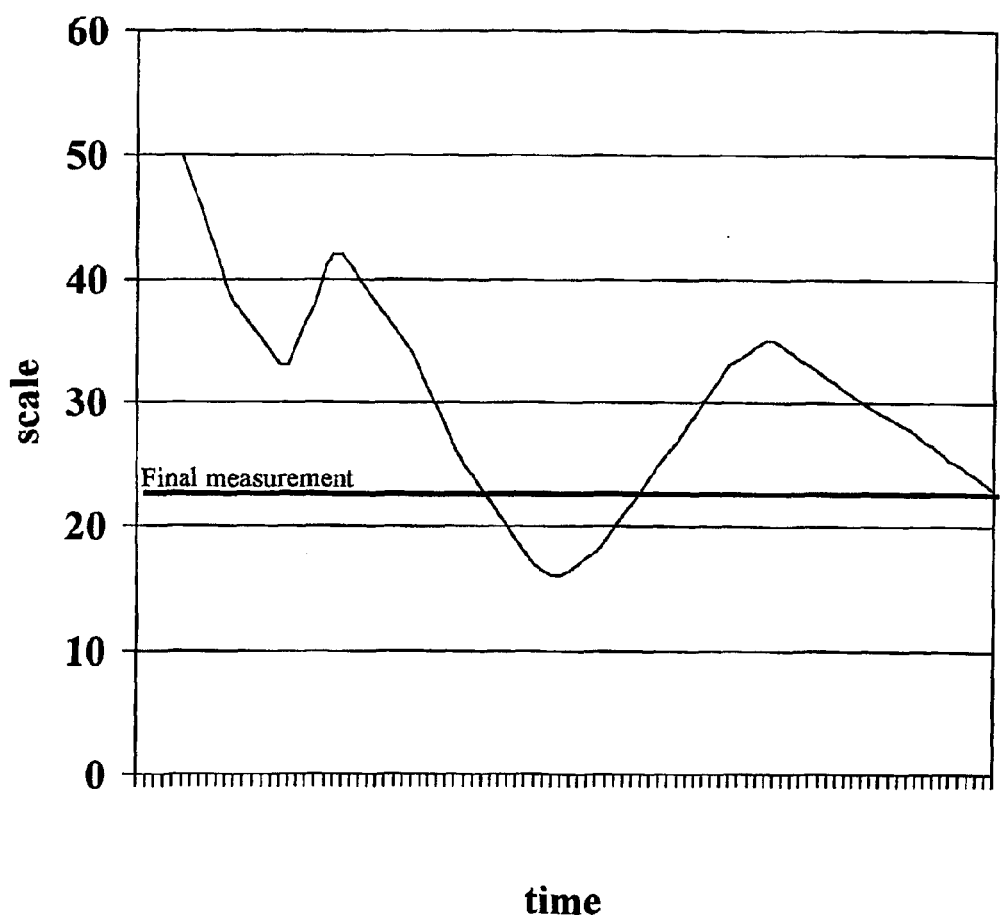
FIG. 5 is a diagrammatic representation of subject reaction to a single question/statement, with or without additional stimuli, yielding the scale position as a function of time.

Upon connection to the network, the measurement data are transferred to the Measurement processing system referring to a single question/statement or to a set of questions/statements. The data are assembled together and stored in the Database 22 in reference to the respective stimuli—see FIG. 1. The data of each measurement are analyzed, and various parameters can be computed. Among them are: the final measurement for each question, the total time interval measured to reach the final measurement for each question, the time interval between the presentation of the stimuli and the first movement of the scale by the subject, the number of events wherein the subject changes his mind and is moving the scale in opposite directions, the range of the scale measurement deviations, the change of the movement speed along the scale, all with reference to the time scale. The complete reaction measurement can be diagrammatically represented as illustrated in FIG. 5.

When multiple measurements are made on one subject, or on a group of subjects, a subject's or subgroup response can be further examined by applying statistical analysis of the measurement parameters like: average, standard deviation, variance and other statistical parameters. In light of these results, the Reaction measurement editor can learn further details on the response of a single or a group of subjects, such as: feelings, judgment, opinion, satisfaction, or involvement towards the stimuli, as well as hesitation, consistency or self confidence of the subject(s). Those outputs might be of great value to the Reaction measurement sponsor. For example in case of an election survey, the results can give more insights regarding hesitant voters or undecided voters.

According to a further embodiment of the present invention it is proposed to enable an online analysis of the subject(s)' reaction and instantaneous response mechanism (feedback) for further questioning of the subject. In order to achieve this goal the measurement process is supplied with two additional functions:

(a) Statistical analysis of the measurements of the subject(s) may result in several additional outcomes such as identifying differences in subjects' reaction to various stimuli, the total time interval for the final reaction (TTF), the time interval until first movement (TFM) etc. Based on these differences one can analyze the subjects not only by final response, but also by the response pattern.

(b) A simplified expert system application (ES Application) enabling the insert of additional stimuli according to pre-defined decision rules. The additional stimuli can contain optional questions for further measurement of the subject's reaction or even presenting open questions. For instance, the measured TTF to a specific question can be compared to the normal average TTF or alternatively to the subject's own average of the TTF. If the TTF is abnormally high, the ES application system can pose a question like: "do you have doubts concerning your last answer?", or "why are you hesitating in your response?"

According to a further embodiment of the present invention it is proposed to enable online inspection of subjects reactions by the Reaction measurement editor. Thus, for example, when conducting mass polls, transmitted online to a large number of subjects, it may be desirable to be able to follow closely and/or trace the subjects' reactions. These features can be implemented in any communication network system, such as the Internet, cellular communication etc., where each of the subject's computerized device is connected to a central server provided with communication software application capable of transmitting and receiving data in real-time. While the subjects are reacting to the stimuli and provide their responses/reactions, all recorded measurements can be transferred to the server. These measurements are gathered by the Measurement processing system, where they are assembled and arranged to create an online presentation of the results. These results can include tables and graphs summarizing various measurements in relation to groups of subjects' reaction to stimuli.

Viewing these results the Reaction measurement editor can locate patterns of the subject(s)' reaction, and in case of unexpected results the editor can intervene immediately and transfer further new stimuli or questions to the subjects, in order to try to better understand and/or explain the phenomenon.

The method and system according to the present invention has a unique combination of advantages:

1. Simplicity, the measurement technique enables a wide spectrum of subjects to respond to different stimuli, independent of their age (4 years and above) and/or educational level, in a simple and intuitive way;
2. Sophistication, the measurement is actually an interval scale, allowing highly sophisticated statistical analysis;
3. Affective, the scale is comprised of a graphical representation which relates to right brain emotional measurement, and as such enables direct measurement of emotions, e.g. feelings, attitudes, pain, preferences;
4. Dynamic, the scale allows the tracing of the complete measurement processes;
5. Reactive, further stimuli can be generated based on an identified response pattern and their analysis;
6. Compatibility, the measurement technique can be adapted to any culture, e.g. color adjustment, or environmental situation, e.g. visibility;

7. Versatility, the measurement application can be implemented in any computerized or communication devices such as: computers, cellular phones, palm devices, interactive TV, etc.;

8. Efficiency, the measurement processing system enables the gathering of data simultaneously from a large number of subjects. When real time response is obtained, the measurement process can provide immediate analysis of the subject(s)' reaction i.e. yielding high time efficiency. Alternatively, when the response is obtained at the subject(s)' convenience it is likely to yield high response efficiency.

While the above description contains many specifities, these should not be construed as limitations on the scope of the invention, but rather as exemplifications of the preferred embodiments. Those skilled in the art will envision other possible variations that are within its scope. Accordingly, the scope of the invention should be determined not by the embodiment illustrated, but by the appended claims and their legal equivalents.

What is claimed is:

1. A method for measuring a subject's reaction to stimuli presentation by using a measurement scale, the method comprising the steps of:
   I. presenting the subject with stimuli and the measurement scale;
   II. enabling the subject to indicate his reaction by moving the position of the scale with reference to time;
   III. tracing and recording the scale positions and movements as a function of time and/or detected measurement events;
   IV. detecting the final scale position; and
   V. evaluating and analyzing the measurement data in order to determine the subject's reaction to the stimuli.

2. The method of claim 1 and further comprising the steps of:
   statistically analyzing any of the measurement data, the measurement events, and the calibrated data; and
   evaluating the subject's reaction to stimuli according to the statistical results.

3. The method of claim 2 and further comprising the step of generating further stimuli based upon analyzing the statistical results and presenting it to the subject.

4. The method of claim 1 and further comprising the step of generating further stimuli based upon the measurement data and presenting it to the subject.

5. The method of claim 1 wherein said steps are applied to more than one subject and further comprising the steps of:
   transferring stimuli to the subjects through communication means;
   gathering and recording measurement data of the subjects in a database; and
   statistically analyzing the measurement data of the subjects' different reactions to the respective stimuli, thereby generating additional statistical results.

6. The method of claim 5 and further comprising the step of generating further stimuli based upon analyzing the additional statistical results and presenting the further stimuli to the subjects.

7. The method of claim 1 wherein the stimuli contain any of questions and statements and are operative to contain an object including any of text, image, audio, video, and smell.

8. The method of claim 1 wherein the measurement scale comprises a defined viewing area having at least one visually distinct area that is proportionate to the subject's reaction.

9. The method of claim 1 wherein the measurement scale is presented by a pendulum, wherein the subject can change the pendulum position within given boundaries.

10. The method of claim 1 wherein the measurement scale is presented initially as a balanced equilibrium, wherein the subject can change the balanced state.

11. The method of claim 1 wherein a measurement event occurs when the subject starts movement of the scale position or stops movement of the scale position or changes in the movement direction or speed.

12. A system for measuring a subject's reaction to stimuli using a measurement scale comprising:
   I. displaying means for presenting stimuli and a measurement scale to a subject;
   II. interface means for changing the scale position;
   III. tracing and recording means for tracing and recording the scale positions and movements as a function of time and/or detected measurement events; and
   IV. computing means for evaluating and analyzing measurement data to determine the subject's reaction to the stimuli.

13. The system of claim 12 and further comprising a feedback module generating further stimuli based upon evaluations and analysis of the measurement data.

14. The system of claim 12 wherein the measurement system is applied to more than one subject and further comprising:
   communication means for transferring stimuli to the subjects;
   memory means for recording measurement data of the subjects in a database; and
   computing means for statistically analyzing the measurement data of the subjects' different reactions to the respective stimuli.

15. The method of claim 14 and further comprising a feedback module for generating further stimuli based upon analyzing the statistical results and presenting the further stimuli to the subjects.

16. The system of claim 12 wherein the stimuli contain any of questions or statements and are presented with a multimedia object including any of text, audio, video and smell.

17. The system of claim 12 wherein the measurement scale comprises a defined viewing area having at least one visually distinct area that is proportionate to the subject's reaction.

18. The system of claim 12 wherein the measurement scale is presented by a pendulum, wherein the subject can change the pendulum position within given boundaries.

19. The system of claim 12 wherein the measurement scale is presented initially as a balanced equilibrium, wherein the subject can change the balanced state.

20. The system of claim 12 wherein a measurement event occurs when the subject starts movement of the scale position or stops movement of the scale position or changes in the movement direction or speed.

21. A system for measuring a subject's reaction to stimuli presentation by using a measurement scale, the method comprising the steps of:
   I. means for presenting the subject with stimuli and the measurement scale;
   II. means for enabling the subject to indicate his reaction by moving the position of the scale with reference to time;
   III. means for tracing and recording the scale positions and movements as a function of time and/or detected measurement events;
   IV. means for detecting the final scale position; and
   V. means for evaluating and analyzing the measurement data in order to determine the subject's reaction to the stimuli.

* * * * *